US00PP29058P2

(12) United States Plant Patent
Eveleens

(10) Patent No.: US PP29,058 P2
(45) Date of Patent: Mar. 6, 2018

(54) ***HYDRANGEA* PLANT NAMED 'HORTFIRE'**

(50) Latin Name: *Hydrangea macrophylla*
Varietal Denomination: Hortfire

(71) Applicants: Horteve Breeding BV, De Kwakel (NL); Kolster Holding BV, Boskoop (NL)

(72) Inventor: Cornelis Pieter Eveleens, De Kwakel (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/330,916

(22) Filed: Nov. 14, 2016

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Penny J. Aguirre

(57) ABSTRACT

A new cultivar of *Hydrangea macrophylla* plant named, 'Hortfire' that is characterized by its picotee sterile flowers with sepals that are white in color with dark pink margins when young and becoming pink in color with similar margins when maturing, its rile flower sepals with wavy crisped margins, and its sterile flower sepals that are purple in color with dark pink picotee margins when grown in acid soil with aluminum sulfate.

2 Drawing Sheets

Botanical classification: *Hydrangea macrophylla.*
Varietal denomination: 'Hortfire'.

CROSS REFERENCE TO A RELATED APPLICATION

This application is co-pending with a U.S. Plant Patent Application filed for a plant derived from the same breeding program that is entitled *Hydrangea* Plant Named 'Horthamp' (U.S. Plant patent application Ser. No. 15/330,917).

BACKGROUND OF THE INVENTION

The present invention relates to a new and distinct cultivar of *Hydrangea macrophylla* and will be referred to hereafter by its cultivar name, 'Hortfire'. 'Hortfire' represents a new bigleaf *hydrangea*, a perennial shrub grown for landscape use.

The objective of the breeding program was to develop new cultivars of *Hydrangea* with sterile flower sepals that are picotee with pink or red edges. 'Hortfire' arose from a controlled cross made by the Inventor in June of 2008 between unnamed and unpatented proprietary plants in the Inventor's breeding program; reference no. 07-036-01 as the female parent and reference no. 07-120-04 as the male parent. 'Hortfire' was initially selected a single unique plant from amongst the resulting seedlings for further evaluation in 2010 and characteristics confirmed in June of 2013.

Asexual propagation of the new cultivar was first accomplished by stem cuttings by the Inventor in Boskoop, The Netherlands in July of 2010. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hortfire' as a unique cultivar of *Hydrangea macrophylla.*

1. 'Hortfire' exhibits picotee sterile flowers with sepals that are white in color with dark pink margins when young and becoming pink in color with similar margins when maturing.
2. 'Hortfire' exhibits sterile flower sepals with wavy crisped margins.
3. 'Hortfire' exhibits sterile flower sepals that are purple in color with dark pink picotee margins when grown in acid soil with aluminum sulfate.

The female parent of 'Hortfire' differs from 'Hortfire' in having a shorter overall plant height and in having sterile flower sepals with entire margins that are not crisped. The male parent of 'Hortfire', differs from 'Hortfire' in having a taller plant size and in having sterile flower sepals with entire margins that are not crisped and that remain white with pink picotee margins as they mature. 'Hortfire' can be most closely compared to the *Hydrangea macrophylla* cultivars 'Hortmaclepa' (U.S. Plant Pat. No. 27,787), 'Hortmaflam' (U.S. Plant Pat. No. 27,716), and 'Horthamp'. These cultivars are similar to 'Hortfire' in having picotee flowers. 'Hortmaclepa' differs from 'Hortfire' in having sterile flower sepals with narrower pink picotee margins and that remain white with pink picotee margins when maturing. 'Hortmaflam' differs from 'Hortfire' in having sterile flower sepals with entire margins that are not crisped and that remain white with pink picotee margins. 'Horthamp' differs from 'Hortfire' in having sterile flower sepals that lacking crisped margins and in having green markings.

BRIEF DESCRIPTION OF THE DRAWINGS

The accompanying colored photographs illustrate the overall appearance and distinct characteristics of the new *Hydrangea*. The photographs were taken of a plant two years in age as grown in a 17-cm container in a greenhouse in Boskoop, The Netherlands.

The photograph in FIG. 1 provides a side view of the plant habit of 'Hortfire' in bloom.

Figure 1:
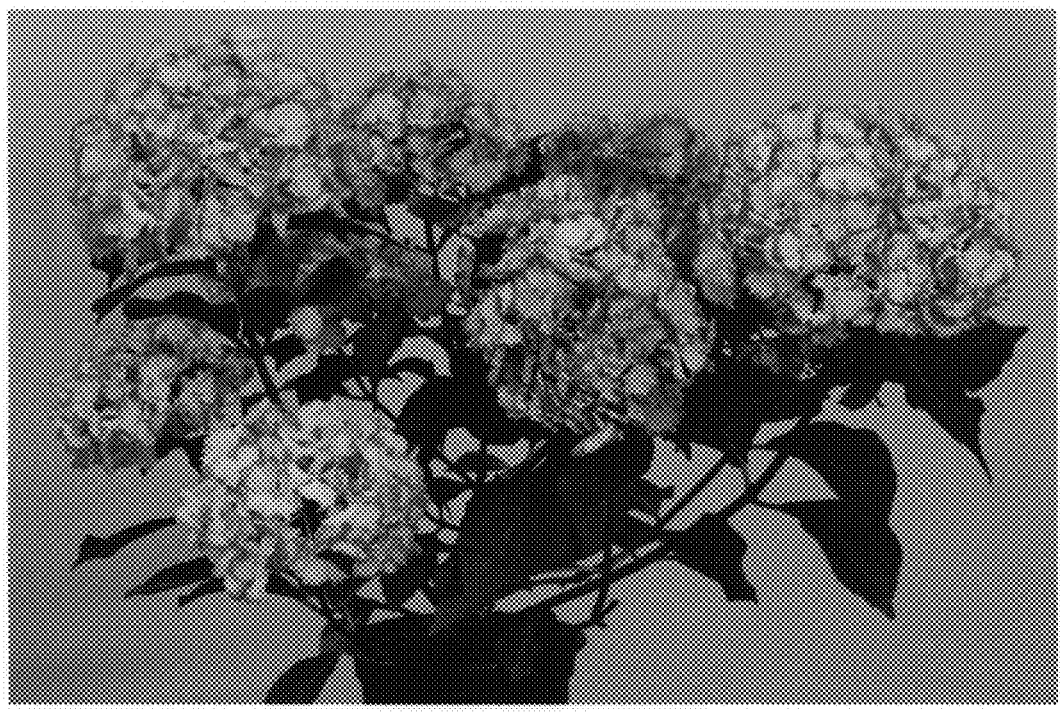
Figure 2:
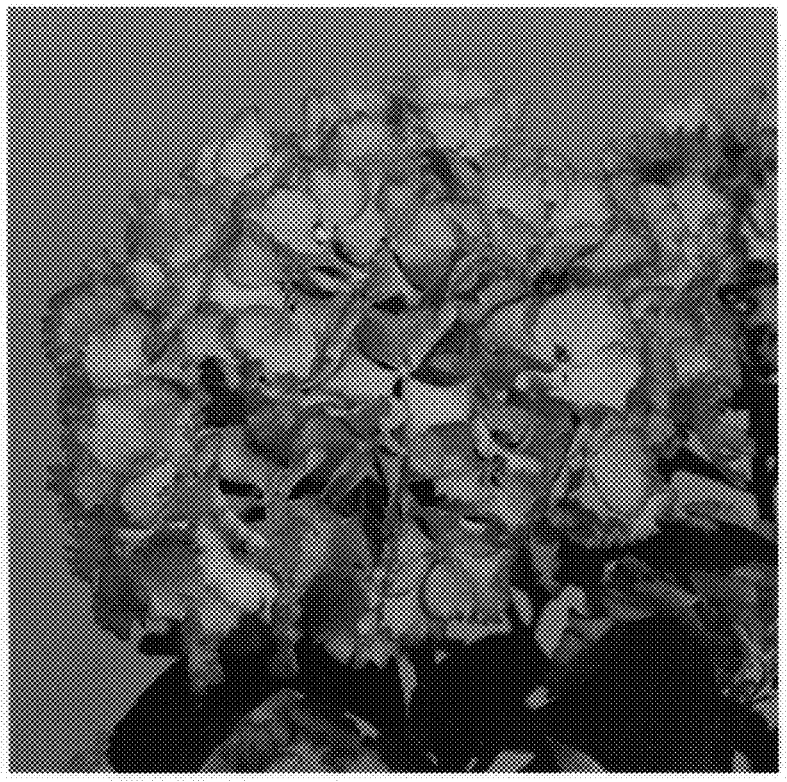

The photograph in FIG. 2 provides a close-up view of a maturing inflorescence of 'Hortfire'.

Figure 3:
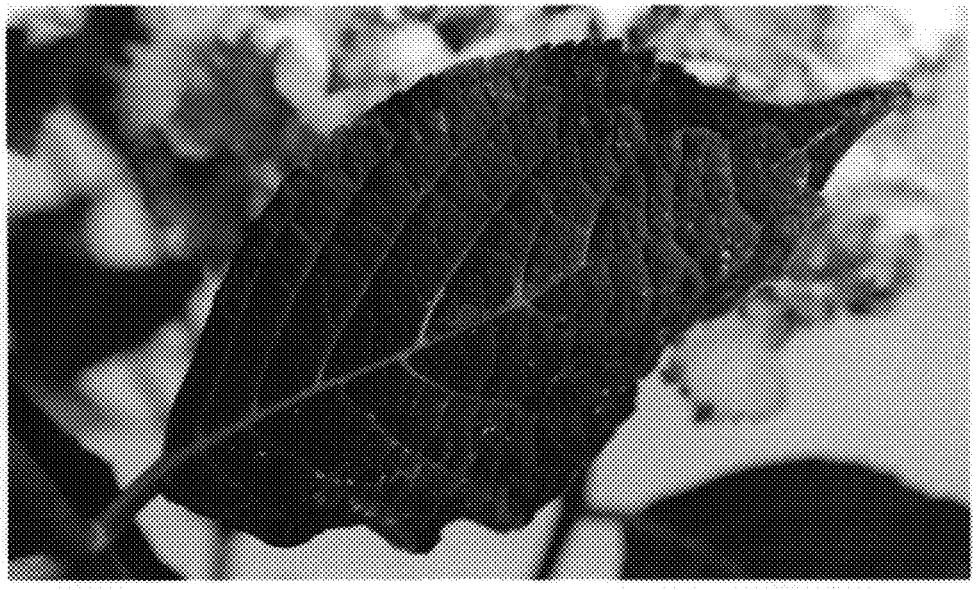

The photograph in FIG. 3 provides a close-up view of a leaf of 'Hortfire'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of plants two years in age as grown in 17-cm containers in a greenhouse in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—From May to July in a greenhouse and from July to September outside in The Netherlands.

*Plant type.*—Perennial shrub, mophead-type *hydrangea.*

*Plant habit.*—Broadly spreading to upright, flattened globular shape.

*Height and spread.*—Up to 1 m in height and 1.5 m in spread after a few years in the landscape.

*Hardiness.*—At least in U.S.D.A. Zones 5 to 9.

*Diseases and pests.*—No susceptibility or resistance to pests and diseases has been observed.

*Root description.*—Fibrous and fine, 177D in color.

*Propagation.*—Stem cuttings.

*Time required for root development.*—An average of 3.5 weeks for root initiation with a young rooted plant produced in an average of six months.

*Growth rate.*—Moderate.

Stem description:

*Stem shape.*—Rounded.

*Stem strength.*—Strong.

*Stem aspect.*—Upright to an average angle of 60° to soil.

*Stem color.*—Immature stems; 144A, mature stems; 144A, older bark; N199C to N199D.

*Stem size.*—An average of 24.7 cm (excluding the inflorescence) in length and 6 mm in diameter.

*Stem surface.*—Immature and mature stems; glabrous and densely lenticellate with lenticels; an average of 2 mm in length and 0.75 mm in width, and N186B to N186C in color.

*Branching.*—Moderately branched with an average of 11 lateral branches, branching improves with pinching.

*Internode length.*—An average of 6.2 cm.

Foliage description:

*Leaf shape.*—Obovate to elliptic.

*Leaf arrangement.*—Opposite.

*Leaf division.*—Simple.

*Leaf number.*—An average of 6 (3 pairs) per lateral branch.

*Leaf base.*—Attenuate.

*Leaf apex.*—Apiculate.

*Leaf margins.*—Serrate.

*Leaf venation.*—Pinnate, color; upper surface 145A and lower surface; 146C.

*Leaf size.*—An average of 12.2 cm in length and 7.5 cm in width.

*Leaf attachment.*—Petiolate.

*Leaf surface.*—Upper surface; smooth, glabrous, and slightly rugose, lower surface; smooth, glabrous, and moderately rugose.

*Leaf color.*—Young leaves; upper surface a blend between 137C and 143A and lower surface; a blend between 146C and 147B, mature leaves; upper surface a blend between NN137A and 189A and lower surface 147B lightly suffused with 203C.

*Petioles.*—An average of 1.3 cm in length and 4 mm in diameter, color; upper surface 144B and lower surface 144A, upper surface; smooth and slightly glossy, lower surface; smooth and moderately glossy.

Inflorescence description:

*Inflorescence type.*—Flattened globular, mophead, compound corymb of rotate-shaped sterile flowers.

*Lastingness of inflorescence.*—Sterile flowers; an average of 6 weeks, sepals persistent, petals self-cleaning, fertile flowers; an average of 1 week, self-cleaning.

*Inflorescence number.*—One per lateral stem.

*Inflorescence size.*—An average of 12.3 cm in height and 19.6 cm in diameter.

*Flower number.*—An average of 125 sterile flowers and 50 fertile flowers per inflorescence.

*Flower fragrance.*—None.

*Flower aspect.*—Sterile flowers; upright and outwards and slightly drooping, fertile flowers; upright.

*Flower size.*—Sterile flowers; an average of 5 cm in diameter and 2.5 cm in depth, fertile flowers; an average of 4 mm in diameter and 3 mm in depth.

*Flower shape.*—Sterile and fertile flowers; rotate.

*Flower buds.*—Sterile flowers; an average of 5 mm in length and 6 mm in diameter, inverted triangle in shape, 145A to 145B suffused with 46A at the apex and margins in color, fertile flowers; an average of 5 mm in length and 3.5 mm diameter, broadly obovate in shape, 155C suffused with 60C at the apex and 145B at the base.

*Peduncles.*—An average of 12 cm in length and 8 mm in diameter, held upright to outwards, 144B in color, smooth surface.

*Pedicels.*—Sterile flowers; an average of 2.4 cm in length and 1.5 mm in diameter, held at an average angle of 40° to peduncle, 73C in color, moderate strength, dull surface is moderately covered with thin hairs an average of 0.2 mm in length and NN155A in color, fertile flowers; an average of 5.5 mm in length and 1 mm in diameter, held at an average angle of 15° to vertical, 145C in color, moderate strength, dull and glabrous surface.

*Petals.*—Sterile flowers; about 4 to 5, rotate, ovate in shape, concave, acute apex, cuneate base, entire margin, an average of 3 mm in length and 2 mm in width, glabrous and dull upper and lower surfaces, color when opening and when fully opened; upper surface NN155D and lower surface NN155D lightly suffused with 75B to 75C, color does not fade, petals drop when mature, fertile flowers; an average of 5, rotate, ovate in shape, concave, acute apex, cuneate base, entire margin, an average of 2 mm in length and 1 mm in width, color; upper surface NN155D and lower surface NN155D slightly suffused with 75B to 75C, petals drop as maturing, both surfaces glabrous and dull.

*Sepals*.—Sterile flowers; an average of 5, rotate in arrangement, reniform in shape, broadly acute to rounded apex, attenuate base, coarsely dentate, crisped margin, an average of 2.8 cm in length and 3.6 cm in width, color; upper and lower surfaces when opening 155A with picotee margin 61C to 61D, upper surface when fully open 73B with picotee margin 60D, lower surface when fully open 73B to 73C with picotee margin 60D, both surfaces; glabrous and dull, fertile flowers; an average of 5, rotate in arrangement, ovate to deltoid in shape, acute apex, broadly cuneate base, entire margin, an average of 1 mm in length and width, color; upper surface when opening and when fully open 145B, lower surface when opening and when fully open 145B fading to 146B towards the apex, colors do not fade, both surfaces glabrous and dull.

Reproductive organs:

*Gynoecium*.—Sterile flowers; 2 pistils, an average of 2 mm in length, stigma; club-shaped and NN155D in color, style; 1 mm in length, NN155B in color, ovary is NN155B in color, fertile flowers; an average of 3 pistils; an average of 1.5 mm in length, stigma; club-shaped and NN155B in color, style; 1 mm in length, NN155B in color, ovary is 145D in color.

*Androecium*.—Sterile flowers; an average of 8 stamens, filaments; an average of 2 mm in length and NN155D in color, anthers; oblong in shape, an average of 0.5 mm in length and NN155B in color, pollen is low in abundance and 155A in color, fertile flowers; an average of 10 stamens, filaments; an average of 2 mm in length and NN150B in color, anthers; broadly reniform in shape, an average of 0.5 mm in length and 203A in color, pollen is low in abundance and 155A in color.

*Fruit and seed*.—No seeds or fruit observed to date.

It is claimed:

1. A new and distinct cultivar of *Hydrangea* plant named 'Hortfire' substantially as herein illustrated and described.

* * * * *